United States Patent [19]

Chou et al.

[11] Patent Number: 5,264,148

[45] Date of Patent: Nov. 23, 1993

[54] MOISTURE SCAVENGING OXAZOLIDINES

[75] Inventors: Chih-Yueh Chou, Elk Grove Village; Arthur T. Jones, Chicago; Thomas L. Johnson, Des Plaines, all of Ill.

[73] Assignee: Angus Cheical Company, Buffalo Grove, Ill.

[21] Appl. No.: 624,062

[22] Filed: Dec. 4, 1990

[51] Int. Cl.$^5$ ................................................ C09K 3/00
[52] U.S. Cl. ..................................... 252/194; 210/698
[58] Field of Search ......................... 252/194; 210/698

[56] References Cited

U.S. PATENT DOCUMENTS

| | | | |
|---|---|---|---|
| 4,199,463 | 4/1980 | Ryer et al. | 548/218 |
| 4,277,353 | 7/1981 | Deen et al. | 252/392 |
| 4,627,932 | 12/1986 | Goel | 252/194 |
| 4,744,950 | 5/1988 | Hollander | 422/16 |
| 4,775,004 | 10/1988 | Shiga et al. | 165/133 |
| 4,944,916 | 7/1990 | Franey | 422/8 |

FOREIGN PATENT DOCUMENTS 3019356 11/1981 Fed. Rep. of Germany.

OTHER PUBLICATIONS

CA 95(24):206550z, "Oil-Soluble Substituted Mono- and Bicyclic Oxazolidines and their Use as Additives for Functional Fluids" Deen et al. (Exxon Research and Engineering Co.), Jul. 1981.
CA 93(12):117076r, "Alkylene Glycol Ester of Carboxylate Half Esters of (1-aza-3,7-dioxabicyclo[3.30]oct-5-yl)methyl Alcohols and Their Use as Additives for Gasoline and Middle Distillate Fuels and Lubricants", Brois et al, (Exxon Research and Engering Co.) Apr. 1980.
Geurink, "Car Refinish Coatings Based On An Oxazolidine-Isocyanate Binder", Cong. FATIPEC, 18th (vol. 2/B), pp. 429-440 (1986).
"Oxazolidine Chemistry and Uses", ANGUS Chemical Company Technical Data Sheet, pp. 1-8 (1991).
Perry, Robert H., "Chemical Engineers Handbook", 5th ed., 1973, pp. 23-59.

Primary Examiner—Richard D. Lovering
Assistant Examiner—Joseph D. Anthony
Attorney, Agent, or Firm—Arnold, White & Durkee

[57] ABSTRACT

The present invention provides a moisture-scavenging composition including the compound:

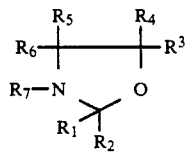

wherein: $R_1$ is a methyl group, or a branched or straight chain alkyl or alkanol group; $R_2$, $R_3$, $R_4$ and $R_6$ are, individually, a hydrogen atom, a methyl group, a straight chain or branched chain alkyl or alkanol group, a cyclic alkyl or an aryl group; $R_5$ is a methyl or methylol group, or a branched chain or straight chain alkyl or alkanol group; $R_7$ is a hydrogen atom, a methyl group, a straight chain or branched chain alkyl or alkanol group, a cyclic alkyl group, a carbonyl group or an aryl group, or $R_7$ and $R_6$ are fused together with the attached carbon to form an eight member bicyclic compound having the structure:

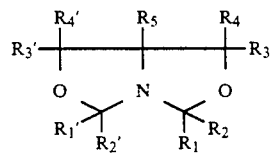

wherein: $R_1'$ is a methyl group or a branched or straight chain alkyl or alkanol group; $R_2'$, $R_3'$, and $R_4'$ are, individually, a hydrogen atom, a methyl group, a straight chain or branched chain alkyl or alkanol group, a cyclic alkyl or an aryl group.

4 Claims, 1 Drawing Sheet

MOISTURE SCAVENGING OXAZOLIDINES

BACKGROUND OF THE INVENTION

1. Field of the Invention

The present invention is generally related to moisture-scavenging compositions, and more particularly, the invention is related to moisture-scavenging oxazolidines.

2. Background of the Art

Moisture-curable polyurethane coatings are extensively used as commercial and industrial protective and/or decorative coatings. Polyurethane coatings, known in the industry as one of the toughest coatings available, are routinely applied as protective coatings on interior and exterior walls of buildings, industrial machinery, military equipment and vehicles, commercial and passenger vehicles, and any other surface requiring a protective coating. Moisture-curable polyurethane systems are also used extensively as sealants and adhesives.

Moisture-curing polyurethane coating systems include a polyisocyanate component which reacts with atmospheric water at room temperature to form useful films. These systems also include pigments, organic solvents, and a variety of adjuvant components, e.g., surface active agents, dispersants, diluents, and fillers. This type of coating is one of the finest coatings available that can be produced without the application of heat or other external sources of energy. These systems are very useful for objects that cannot be heat-cured such as buildings, large machinery, airplanes, ships and vehicles.

Since the polyisocyanate component reacts with even trace amounts of moisture, extreme care must be taken so that the polyisocyanates do not contact water until they are applied to a surface to be coated. Water is, however, unintentionally and unavoidably introduced into the formulation process in the form of dissolved water in solvents, adsorbed and absorbed water in fillers and pigments, and atmospheric moisture. Subsequent reaction of the water with the polyisocyanate component of the system results in an irreversible reaction which will harden the product, making it unusable before it can be applied to the surface to be coated.

Moisture-curing polyurethane coatings are supplied as both one and two-part systems. In a two-part system, a polyol is chosen that will chemically react with and polymerize the polyisocyanate. The polyol portion generally includes a pigment. The pigmented polyol portion and the polyisocyanate portion are supplied in separate containers to the ultimate user or consumer. The consumer mixes the two portions in accordance with the ratio specified by the manufacturer just prior to use. This admixture has a limited life and must be used within a relatively short period of time or it will polymerize and become unusable in its container.

The two-part system presents several problems to the ultimate user. For example, there is a risk that the pigmented polyol portion and the polyisocyanate portion will not be mixed in the correct ratio. This could seriously detract from the performance of the resulting moisture-cured polyurethane coating. In addition, this approach is expensive in that material is wasted if the entire admixture is not used promptly.

Moisture-curing polyurethane coatings are also supplied as a one-part system eliminating all of the above mentioned problems of the two-part system. In the one-part system, however, extreme care must be taken to assure that all of the moisture is removed from the system prior to packaging the product; otherwise, the polyisocyanate component in the product will react with the available water and polymerize in the container. Sources of water in one-part systems include color pigments and fillers which contain adsorbed moisture on their surfaces, water dissolved in solvents, and atmospheric moisture. This water must be removed in order to produce an acceptable product. The existing methods for preparing color-pigmented moisture-curable polyurethane coatings in a single package require expensive equipment to dry the pigments, solvents, and fillers. In the alternative, moisture-scavenging agents are added to the preparation.

One group of moisture-scavenging compounds are the molecular sieves. Molecular sieves adsorb water into their pores, thereby binding the water and preventing it from reacting with the polyisocyanate component. An example of a molecular sieve is sodium potassium aluminosilicate, available from the Mobay Corp., Pittsburgh, Pa., under the tradename designation Baylith L Powder. One disadvantage of using molecular sieves is that they reduce the gloss of the cured coating. Another disadvantage of molecular sieves is that they will sometimes plasticize or embrittle the cured coating.

A second group of water-scavenging agents widely used to prevent moisture-contamination of moisture-curable polyurethane coating systems is the monomeric isocyanates. The monomeric isocyanates, such as p-toluenesulfonyl isocyanate (Vanchem, Inc. Lockport, Conn.), react with water to generate carbon dioxide and the corresponding sulfonamide, e.g., p-toluenesulfonamide. The carbon dioxide diffuses from the curing coating as carbon dioxide gas.

A disadvantage of monomeric isocyanates is that they are extremely corrosive to skin and toxic. In literature prepared by a supplier of monomeric isocyanates (Aldrich Chemical Co., Milwaukee, Wis.), monomeric isocyanates are referred to as harmful if swallowed, inhaled, or absorbed through the skin. Moreover, these compounds are listed as extremely corrosive to the tissues of the mucous membranes, upper respiratory tract, and skin. Symptoms of monomeric isocyanate exposure include burning, coughing, nausea and vomiting, chemically induced asthma, chest pain, and pulmonary edema possibly causing death. If these compounds are to be handled by the ultimate user, the manufacturer recommends a self-contained breathing apparatus, rubber boots and heavy rubber gloves. Since these compounds are extremely corrosive to skin and toxic, great care must be taken in their manufacture, handling, and use. This enormous health risk dramatically increases the cost of these compounds to the manufacturer and the ultimate user.

There is a need for a moisture-scavenger which efficiently, cost effectively, and safely removes water from moisture-curable polyurethane coating systems and from any other application where residual water is a problem, without seriously detracting from the performance of the cured coating.

SUMMARY OF THE INVENTION

In order to satisfy the need for an efficient, cost effective and lower toxicity moisture-scavenger, one aspect of the present invention provides a moisture-scavenging composition including the compound:

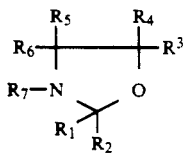

wherein: $R_1$ is a methyl group, a branched or straight chain alkyl or alkanol group; $R_2$, $R_3$, $R_4$ and $R_6$ are, individually, a hydrogen atom, a methyl or group, a straight chain or branched chain alkyl or alkanol group, a cyclic alkyl, or an aryl group; $R_5$ is a methyl or methylol group, or a branched chain or straight chain alkyl or alkanol group; $R_7$ is a hydrogen atom, a straight chain or branched chain alkyl or alkanol group, a cyclic alkyl group, a carbonyl group, or an aryl group, or $R_7$ and $R_6$ are fused together with the attached carbon to form an eight member bicyclic compound having the structure:

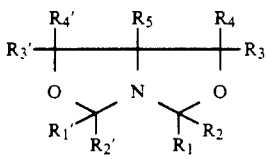

wherein: $R_1'$ is a methyl group, a branched or straight chainalkyl or alkanol group; $R_2'$, $R_3'$, and $R_4'$ are, individually, a hydrogen atom, a methyl group, a straight chain or branched chain alkyl or alkanol group, a cyclic alkyl, or an aryl group; and $R_5$ is a methyl or methylol group, or a branched chain or straight chain alkyl or alkanol group.

In a preferred embodiment, the $R_7$ substituent of the compound is a hydrogen atom, a methyl group, a straight chain or branched chain alkyl or alkanol group, or a carbonyl group. The $R_5$ substituent is a branched chain or straight chain alkyl or alkanol group. The $R_3$ substituent of the compound is a hydrogen, a methyl group, or a ($C_2$-$C_5$) straight or branched chain alkyl or alkanol group. The $R_6$ and $R_4$ groups are a hydrogen atom. The $R_1$ substituent is a methyl group, or a ($C_2$-$C_5$) branched or straight chain alkyl or alkanol group, and the $R_2$ substituent is a hydrogen atom.

In another preferred embodiment of the invention, the $R_6$ and $R_7$ substituents are fused together with the attached carbon to form the eight member bicyclic compound. The $R_1$ and $R_1'$ substituents are, individually, a methyl group, or a ($C_2$-$C_5$) straight or branched chain alkyl or alkanol group. The $R_2$, $R_2'$, $R_3$, $R_3'$, $R_4$ and $R_4'$ substituent groups are, individually, a hydrogen atom. The $R_5$ substituent group is a methyl group, or a ($C_2$-$C_5$) straight or branched chain alkyl or alkanol group.

A further aspect of the invention is directed to a method of dehydrating a preparation. According to the method, an effective amount of the moisture-scavenging composition including at least one of the compounds described above is intimately admixed with the preparation. In one preferred embodiment, the compound is a monocyclic moisture-scavenger and the effective amount of the composition includes from 1 to 3 moles of the moisture-scavenging compound for every mole of water in the preparation to be dehydrated. In another preferred embodiment, the compound is a bicyclic moisture-scavenger and the effective amount of the composition includes from 0.5 to 2 moles of the moisture-scavenging compound for every mole of water in the preparation to be dehydrated.

The moisture-scavenging compositions of the invention can consist entirely of the moisture-scavenging compound described above. In the alternative, the composition can include an effective amount of pigments, organic solvents, fillers, polyisocyanates and adjuvants. The amount of the moisture-scavenging compounds included in the composition is critical to the invention to the extent that the composition must include a sufficient amount of the moisture-scavenging compound to dehydrate the preparation to which it is added to, e.g., an organic solvent, or a pigment millbase preparation. Furthermore, the composition must contain a sufficient amount of the moisture-scavenger compound to prepare anhydrous compositions useful in applications in which water is preferably avoided, e.g., moisture-curable polyurethane applications, or dehydration of surfaces onto which moisture-curable coating are to be applied.

DESCRIPTION OF THE PREFERRED EMBODIMENT

Figure 1:
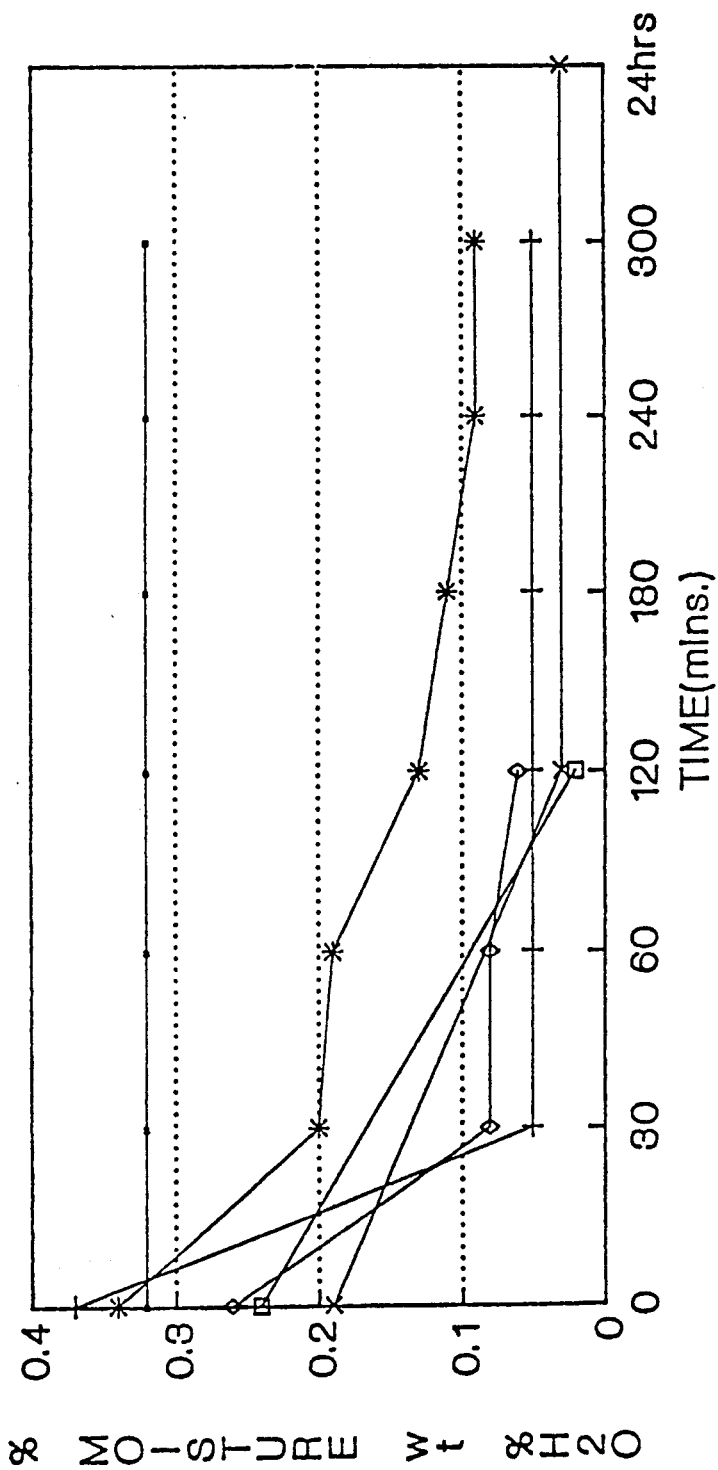
FIG. 1 graphically illustrates the moisture-scavenging activity of 4-ethyl-2-isopropyl oxazolidine (BBA) (✲), 1-aza-3,7-dioxo-2,8-diisopropyl-5-ethyl-bicyclo (3.3.0) octane (EBA) (◇), p-toluenesulfonyl isocyanate (PTSI) (+), isophorone diisocyanate (IPDI) (□), sodium potassium aluminosilicate (SPAS) (✻), and a control (■).

The present invention provides a moisture-scavenging composition including a new class of moisture-scavenging compounds. The composition can be advantageously used in the formulation of specialty moisture-curable polyurethane systems, including sealants, adhesives and coatings, and in any other application in which residual water is a problem. It has been discovered that a class of compounds including substituted monocyclic and bicyclic oxazolidines are excellent moisture-scavengers. The prior art has disclosed a rather broad class of oxazolidine compounds as crosslinking reagents, reacting with polyfunctional isocyanates in the presence of polyols or water to form polymeric coatings. U.S. Pat. No. 4,101,527 discloses an equimolar reaction of an oxazolidine with a polyfunctional isocyanate in the presence of water to form a polyurethane coating.

The moisture-scavenging composition of the present invention includes the compound:

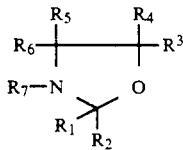

wherein: $R_1$ is a methyl group, or a branched or straight chain alkyl or alkanol group; $R_2$, $R_3$, $R_4$ and $R_6$ are, individually, a hydrogen atom, a methyl group, a straight chain or branched chain alkyl or alkanol group, a cyclic alkyl, or an aryl group; $R_5$ is a methyl or methylol group, or a branched chain or straight chain alkyl or alkanol group; $R_7$ is a hydrogen atom, a straight chain or branched chain alkyl or alkanol group, a cyclic alkyl group, a carbonyl group, or an aryl group, or $R_7$ and $R_6$ are fused together with the attached carbon to form an eight member bicyclic compound having the structure:

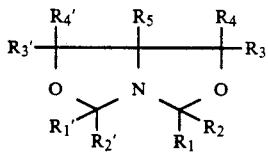

wherein: $R_1'$ is a methyl group, or a branched or straight chain alkyl or alkanol group; $R_2'$, $R_3'$, and $R_4'$ are, individually, a hydrogen atom, a methyl group, a straight chain or branched chain alkyl or alkanol group, a cyclic alkyl, or an aryl group.

Referring to the monocyclic moisture-scavenging oxazolidines of the present invention, the preferred R group substituents are those which increase the reactivity of the ring to water. Without limiting the invention, it has been discovered that aliphatic or aromatic R group substituents increase the reactivity of the ring to water. The monocyclic moisture-scavenging oxazolidine compounds of the present invention react chemically with water in the following manner:

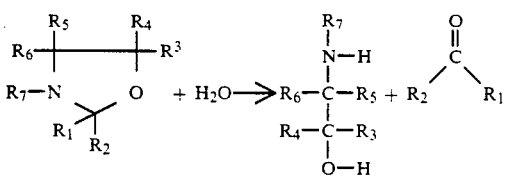

As shown above, the reaction products are an amino alcohol and a carbonyl compound. One mole of monocyclic moisture-scavenging oxazolidine will react with and remove one mole of water. Therefore, it is preferred that the moisture-scavenging compositions of the invention containing monocyclic oxazolidines include at least one mole of the monocyclic moisture-scavenging oxazolidine for each mole of water to be removed. However, since a perfectly efficient reaction environment cannot be guaranteed in industrial settings, it is preferable that from 1 to about 3 moles of the moisture-scavenging monocyclic oxazolidine be included for every mole of water to be removed. Greater amounts of the monocyclic oxazolidine can be added, but are not preferred.

All R group substituents which facilitate the reaction of water with the monocyclic moisture-scavenging oxazolidines of the present invention are preferred. In one preferred embodiment of the invention, the $R_3$ substituent of the compound is a hydrogen atom, a methyl group, or a ($C_2$–$C_5$) straight or branched chain alkyl or alkanol group; the $R_4$ substituent is a hydrogen atom; the $R_1$ substituent is a methyl group or a ($C_2$–$C_5$) branched or straight chain alkyl or alkanol group; the $R_2$ substituent is a hydrogen atom; the $R_6$ substituent is a hydrogen atom; the $R_5$ substituent is a methyl group or a branched or straight chain alkyl or alkanol group; and the $R_7$ substituent is a hydrogen atom, a carbonyl group or a straight or branched chain alkyl or alkanol group. More preferably, the $R_1$ substituent of the compound is a ($C_2$–$C_5$) straight or branched chain alkyl or alkanol group; the $R_2$, $R_3$, $R_4$ and $R_6$ substituents are hydrogen atoms; the $R_7$ substituent is a carbonyl group or a ($C_2$–$C_5$) straight chain or branched chain alkyl or alkanol group; and the $R_5$ substituent is a methyl group or a ($C_2$–$C_5$) branched or straight chain alkyl or alkanol group. Most preferably, the $R_1$ substituent is an isopropyl group; the $R_2$, $R_3$, $R_4$ and $R_6$ substituents are a hydrogen atom; the $R_7$ substituent is a carbonyl group or a ($C_2$–$C_3$) straight chain or branched chain alkyl group; and the $R_5$ substituent is a ($C_2$–$C_4$) branched or straight chain alkyl or alkanol group.

In another preferred embodiment of the invention, the $R_4$ and $R_7$ substituents are fused together with the attached carbon to form the eight-member bicyclic compound shown above. Similarly to the monocyclic moisture-scavenging oxazolidines, in the bicyclic moisture-scavenging oxazolidines the preferred R group substituents are those which increase the reactivity of the rings to water. Illustrated below is the reaction of the bicyclic moisture-scavenging oxazolidines with water:

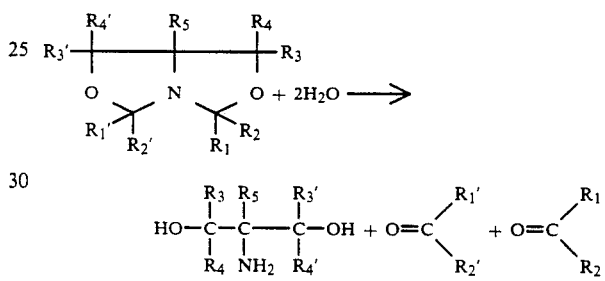

Similarly to the monocyclic moisture-scavenging oxazolidines of the invention, the reaction products are an amino alcohol and a carbonyl compound. One mole of bicyclic moisture-scavenging oxazolidine will react with and remove two moles of water. Therefore, it is preferred that the moisture-scavenging compositions of the invention containing bicyclic oxazolidines include at least one-half mole of the bicyclic moisture-scavenging oxazolidine for each mole of water to be removed. As discussed above, since a perfectly efficient reaction environment cannot be guaranteed in industrial settings, it is preferable that from 0.5 to about 2 moles of the moisture-scavenging bicyclic oxazolidine be included in the inventive composition for every mole of water to be removed. Greater amounts of moisture-scavenging bicyclic oxazolidine can be included, but are not preferred.

R group substituents which facilitate the reaction of water with the bicyclic moisture-scavenging oxazolidines of the present invention are preferred. According to one preferred embodiment, the $R_1$ and $R_1'$ substituents are, individually, a methyl group or a ($C_2$–$C_5$) straight or branched chain alkyl or alkanol group; the $R_2$, $R_2'$ $R_3$, $R_3'$, $R_4$ and $R_4'$ substituent groups are hydrogen atoms; and the $R5$ substituent group is a methyl group or a ($C_2$–$C_5$) straight or branched chain alkyl or alkanol group. According to another preferred embodiment, the $R_1$ and $R_1'$ substituents are isopropyl groups.

The structure of the R substituents in either the monocyclic or bicyclic oxazolidines is determined by the selection of the reactant precursor compounds. The oxazolidines of the present invention are prepared by reacting a primary amino alcohol with a carbonyl compound. In a specific embodiment of the invention, 4-ethyl-2-isopropyl oxazolidine is prepared by reacting 2-amino-1-butanol with isobutyraldehyde. Detailed protocols for synthesizing several preferred moisture-scavengers of the present invention are described herein.

A further aspect of the invention is directed to a method of dehydrating a preparation. In one embodiment the preparation includes at least one pigment and at least one organic solvent. According to the method, an effective amount of the composition of the invention including a bicyclic or monocyclic oxazolidine moisture-scavenging compound described above is intimately admixed with the preparation. In one preferred embodiment, the effective amount includes from 1 to about 3 moles of a monocyclic oxazolidine moisture-scavenging compound for every mole of water in the preparation to be dehydrated. In another preferred embodiment, the effective amount includes from about .5 to about 2 moles of a bicyclic moisture-scavenging oxazolidine for every mole of water in the preparation to be dehydrated.

According to one embodiment of the invention, catalysts are added in combination with the moisture-scavenging monocyclic or bicyclic oxazolidines of the present invention to facilitate the reaction with water. The addition of a preferred catalyst will, in some instances, minimize the amount of the oxazolidine required to remove water from a preparation by increasing the efficiency of the reaction. Furthermore, a preferred catalyst will, in certain circumstances, increase the rate at which the moisture-scavenging oxazolidines react with water. Preferred catalysts include the organometallic catalysts and the acid catalysts.

According to another embodiment of the invention, the reaction between the moisture-scavenging oxazolidines and water occurs at temperatures from ambient to about the boiling point of the preparation being dehydrated. Preferably, this range is from about 60 to about 160 degrees Fahrenheit. Increasing the temperature at which the reaction occurs increases the rate and the efficiency of the reaction.

The moisture-scavenging compounds of the present invention are advantageously used in urethane coating, sealant and adhesive systems to remove moisture during the formulation, packaging and application steps. The present invention provides the producer of specialty polyurethane systems with an expedient and efficient alternative to the physical methods of dehydration, exemplified by molecular sieves and drying machinery, and the potentially toxic prior chemical methods, exemplified by the monomeric isocyanates presently available. The moisture-scavenging compositions of the present invention are further provided for the storage stabilization of moisture-curable polyurethane systems. A still further intended use of the invention is the dehydration of surfaces onto which moisture-curable coatings are to be applied.

The invention provides an anhydrous composition including the moisture-scavenging compounds described above and an organic solvent. Solvents used in the formulation of one and two-component systems are rapidly dehydrated by treating them with the moisture-scavenging composition of the invention. This anhydrous composition is useful in any application where water is preferably avoided, e.g., preparing moisture-curable polyurethane coatings, or dehydrating surfaces prior to applying moisture-curable coatings. The quantity of moisture-scavenger in the composition will vary with the water content of the solvent. The amount of water in the organic solvent being dehydrated can be determined by gas chromatography. The solvents generally used in the formulation of specialty polyurethane systems are compatible with the moisture-scavenging compositions of the present invention. Solvents generally used in the preparation of polyurethane moisture-scavenging preparations include aprotic solvents, such as ketones, esters, ethers, nitroparaffins, glycol esters, glycol ether esters, halogenated hydrocarbons, and alkyl and aromatic hydrocarbons.

Pigments, fillers, polyisocyanates, and adjuvants are suspended in organic solvents. For the purposes of this invention the term "fillers" is intended to include those materials added to a coating preparation to increase the solids content of the coating. The term "adjuvants" is intended to include those materials which are added to the coating formulation to aid application or formation, such as surface active agents, anti-settling agents, diluents, suspending agents and the like. Pigments, fillers, polyisocyanates and adjuvants can also be dehydrated with the water-scavenging compositions of the present invention. One aspect of the invention is a substantially anhydrous composition including pigments, fillers, organic solvents, and the moisture-scavenging compounds described above. It has been determined that a reaction period of from 30 minutes to about twenty-four hours is preferred to ensure substantially complete dehydration of pigment preparations. The amount of the moisture-scavenger composition required to dehydrate the pigment or filler will vary with the total water content. Through the addition of the moisture-scavenging composition of the invention, an anhydrous composition is produced including pigments, organic solvent(s), fillers, polyisocyanates and adjuvants. Alternatively, any of the above-listed components can be deleted, depending on the needs of the ultimate user. This anhydrous composition is useful in applications where water is preferably avoided, e.g., in the formulation of moisture-curable polyurethane coatings.

The following examples are presented to describe preferred embodiments and utilities of the present invention and are not meant to limit the present invention unless otherwise stated in the claims appended hereto.

EXAMPLES

Example 1

Preparation of 4-ethyl-2-isopropyl oxazolidine

To a 12-liter, 4-neck, round bottom flask equipped with a mechanical stirrer, a 1-liter addition funnel, and a Dean-Stark receiver (500 ml. capacity) was added D,L-2-amino-1-butanol (4,001 grams; 44.21 mol.; 98.5% pure). The flask was rapidly stirred and maintained under a nitrogen atmosphere. Thereafter, isobutyraldehyde (3,478 grams.; 47.27 mol.; 98% pure) was added through the 1-liter addition funnel over a period of 1.2 hours. After the addition of the isobutyraldehyde was completed, the reactor and the Dean-Stark receiver Was insulated with glass wool and the mixture Was heated. The reaction mixture was heated to reflux continuously for 10 hours. After a total of 787 grams of Water was removed, the reaction mixture was cooled down to about 70° C. The Dean-Stark trap was replaced with a vacuum distillation apparatus including: a distilling column; an adaptor; two condensers (1 Fredericks and 1 Allihn type); and a vacuum adaptor. An aspiration pump was used for vacuum stripping at a pressure of 40 to about 45 mmHg. The vacuum was maintained for about 4 hours, and a total of 273 grams of liquid was removed, 43 grams of which was water and 230 grams was organic material, mainly isobutyraldehyde. After the vacuum stripping operation was completed, a yellow liquid (6,314 gram.) was obtained. Gas chromatographic analysis demonstrated that 93.01% of this liquid was the product 4-ethyl-2-isopropyl oxazolidine.

Example 2

Preparation of 1-aza-3,7-dioxo-2,8-diisopropyl-5-ethyl bicyclo (3.3.0) octane

In a 12-liter, 4-neck, round-bottom flask equipped with a 1-liter addition funnel and a Dean-Stark receiver, (500 ml. liter capacity) was charged with 2-amino-2-ethyl-1, 3propanediol (3,618 grams; 30.29 mol.) under a nitrogen-atmosphere. The liquid was rapidly stirred. To the liquid, isobutyraldehyde (4,468 grams; 60.72 mol.; 98% pure) was added through the 1-liter addition funnel over a period of 115 minutes. After the addition of the isobutyraldehyde was completed, the reactor and the Dean-Stark receiver were insulated with glass wool, and heating was started. The reaction mixture was heated to reflux continuously for about 24 hours. After this time, a total of 1,060 grams of water had been removed. Thereafter, the reaction mixture was allowed to cool overnight. Vacuum stripping to remove any remaining water and any excess isobutyraldehyde was initiated at 40–45 mmHg, and continued for 5 hours. During this procedure, a total of 364 grams of liquid (two layers) was removed, 51 grams of which was water and 313 grams of which was organic liquid (mainly isobutyraldehyde). After the vacuum stripping was completed, 6,558.7 grams of a yellow liquid With a few specks of tan colored solid was obtained. Gas chromatographic analysis showed that 86.88% of this remaining liquid was 1-aza-3,7-dioxo-2,8-bicyclo-diisopropyl-5-ethyl (3.3.0) octane.

Example 3

Comparison of Water-Scavenging Activity

The water-scavenging activity of 4-ethyl-2-isopropyl oxazolidine (BBA), 1-aza-3,7-dioxo-2,8-diisopropyl-5-ethylbicyclo (3.3.0) octane (EBA), p-toluenesulfonyl isocyanate (PTSI), isophorone diisocyanate (IPDI), and sodium potassium aluminosilicate (SPAS) were compared in pigment millbase formulation. Formulations of this type are representative of pigment formulations used in moisture-curing urethane coating systems. The following millbase formulation was used:

| MILLBASE | WEIGHT (GRAMS) |
| --- | --- |
| Soft Resin P-65 | 338.50 |
| 33% CAB 551 in PMA | 94.50 |
| Anti-Terra-U | 10.00 |
| Ektasolve EEP | 188.00 |
| Xylene | 195.50 |
| M-P-A 2000 X | 50.00 |
| R-960 TiO$_2$ | 1,420.50 |
| Total Weight = | 2,297.00 |

The following procedure was used to prepare the millbase. All the materials were weighed out and added under agitation into a pot. Soft Resin P-65, obtained from Mobay Corp., is a 65% synthetic (non-reactive polyester) resin in solvent Naphtha 100 and is employed as a grind aid. CAB 551, obtained from Eastman Chemical Products, Inc., Kingsport, Tenn., is cellulose acetate butyrate ester and was employed as a rheology aid. CAB 551 was dissolved in PMA. PMA is propylene glycol monomethyl ether acetate obtained from Eastman Chemical Products, Inc. The solution of CAB 551 in PMA included 33% CAB 551 by weight. Anti-Terra-U is a wetting and dispersing additive obtained from BYK-Chemie U.S.A., Wallingford Conn., and is a solution of a salt of unsaturated polyamine amides and higher molecular weight acidic esters. Ektasolve-EEP, obtained from Eastman Chemicals Products, Inc., is ethyl-3-ethoxypropionate stabilized with 2,6-di-tert-butyl- p-cresol, and was employed as a solvent. M-P-A 2000X, obtained from Rheox, Inc., Hightstown, N.J., was employed as an antisettling agent. R-960-TiO$_2$ is a titanium dioxide pigment obtained from E.I. du Pont Nemours & Co., Inc., Wilmington, Del.

Once the ingredients were added to the vessel they were continuously agitated until a 7 Hegman grind value was obtained for the mixture. The millbase was then heated to 60° C. A portion of the mixture was removed, and the percent of water remaining was determined using gas chromatography. Using the determined percentage of water, the minimum amount of the water-scavenger compound to be added to the millbase was calculated using the following equation:

$$\text{Minimum weight of water scavenger} = \text{wt. mb.} \times \text{wt. \% H}_2\text{O} \times (1/\text{MW H}_2\text{O} \times \text{mol.} \times \text{MW scavenger/purity})$$

wt. mb. = the total weight for the millbase;
weight % H$_2$O = GC calculated value for the millbase;
MW = molecular weight of the material used;
mol. = minimum number of moles moisture scavenger required purity = % assay of material used.

The determined amount of each moisture-scavenger was added to one millbase. Six millbases were prepared. Each of the five moisture-scavengers listed above were tested in a millbase with one millbase remaining untreated as a control. Once the millbases were treated, they were mixed continuously. At 30 minutes, 60 minutes, 120 minutes, 180 minutes, 240 minutes, and 300 minutes, samples of the millbase were removed and the amount of water remaining in the millbase was determined using gas chromatography. In each trial two moles of moisture scavenger was used for every mole of water. The results of 6 trials are summarized below in Table I and graphically represented in FIG. 1.

| Trial No. | Systems | Weight % Water In Untreated Millbase | % H$_2$O Remaining After 30 min. | 60 min. | 2 hrs. |
| --- | --- | --- | --- | --- | --- |
| 1 | No scavenger | .32 | .32 | .32 | .32 |
| 2 | PTSI | .37 | <.05 | <.05 | <.05 |
| 3 | IPDI | .24 | | | <.02 |
| 4 | SPAS | .19 | | | <.03 |
| 5 | BBA | .34 | .20 | .19 | .13 |
| 6 | EBA | .26 | .08 | .08 | .06 |

Example 4

Mutagenicity of 2-isopropyl-4-ethyl oxazolidine

The Ames Mutagenicity Assay was performed to determine the mutagenicity of the compound. The assay evaluates the mutagenic potential of a test substance by its ability to induce back mutations at selected loci of four strains of *Salmonella typhimurium* in the presence and absence of an exogenous mammalian activation system. The results of the assay indicated that 2-isopropyl-4-ethyl oxazolidine is non-mutagenic.

Example 5

Acute Oral Toxicity of 2-isopropyl-4-ethyl

Based upon the standards of the Toxic Substance Control Act (TSCA), 40 CFR, Part 798, Subpart A, General Toxicity Testing, Acute Oral Toxicity, 798.1175, July 1989, 2-isopropyl-4-ethyl oxazolidine was evaluated for its potential to produce death following oral administration at dose levels of 1.80g/kg, 1.50 g/kg, and 1.30 g/kg, to male and female Sprague-Dawley rates. Based upon mortality, the $LD_{50}$ was calculated at 1.60 g/kg.

Example 6

Primary Dermal Irritation of 2-isopropyl-4-ethyl oxazolidine

Based upon the standards of the Toxic Substances Control Act (TSCA), 40 CFR, Part 798, Subpart E, Specific Organ/Tissue Toxicity, Primary Dermal Irritation, Section 798.4470, July 1989, 2-isopropyl-4-ethyl oxazolidine was evaluated for its potential to produce primary dermal irritation after a single topical application to the skin of New Zealand White Rabbits. The compound was considered a moderate irritant according to the TSCA guidelines.

Example 7

Acute Dermal Toxicity of 2-isopropyl-4-ethyl oxazolidine

Based upon the standards of the Toxic Substance Control Act (TSCA), 40 CFR, Part 798, Subpart A, General Toxicity Testing, Acute Dermal Toxicity, 789.1100, July 1989, the compound was evaluated for its potential to produce systematic toxicity or death following topical application at a dose of 2 g/Kg in male and female New Zealand White albino rabbits. Based on the absence of mortality and the criteria of the study protocol, the test substance was defined as non-toxic according to TSCA guidelines; however, the test substance was corrosive to the skin following a 24 hr. exposure.

Example 8

Mutagenicity of 1-aza-3,7-dioxo-2,8-bicyclodiisopropyl-5-ethyl (3.3.0) octane The Ames Mutagenicity Assay was performed to determine the mutagenicity of the compound. The assay evaluates the mutagenic potential of a test substance by its ability to induce back mutations at selected loci of four strains of Salmonella typhimurium in the presence and absence of an exogenous mammalian activation system. The results of the assay indicated that the compound is non-mutagenic.

Example 9

Acute Oral Toxicity of 1-aza-3,7-dioxo-2,8-bicyclodiisopropyl-5-ethyl (3.3.0) octane The acute oral toxicity of the compound was evaluated in compliance with the conditions specified in the Regulation for the Enforcement of Federal Insecticide, Fungicide and Rodenticide Act (40 CFR 162). The compound was administered undiluted at a dosage of 5.0 g/kg to one group of five male and five female, Sprague-Dawley derived, albino rats. The animals were observed for gross signs of toxicity and death for 14 days. Animals were weighed seven days after treatment. At the end of the 14-day observation period, the rats were weighed, killed, and given a gross necropsy.

No deaths occurred during the observation period. Clinical changes associated with the test material included urine and/or fecal stains, mucoid feces, and alopecia. Gross necropsies performed at the end of the study revealed one rat with darkened and mottled lungs, otherwise no gross changes. The acute oral $LD_{50}$ value was found to be greater than 5.0 g/kg in male and female Sprague-Dawley rats. The material was classified in Toxicity Category IV by oral administration.

Example 10

Acute Dermal Toxicity of 1-aza-3,7-dioxo-2,8-bicyclo-diisopropyl-5-ethyl (3.3.0) octane The acute dermal toxicity of the compound was evaluated in compliance with the conditions specified in the Regulation for the Enforcement of Federal Insecticide, Fungicide and Rodenticide Act (40 CFR 162). The compound was applied undiluted to the skin of one group of five male and five female New Zealand White Rabbits at a dosage of 2.0 g/kg for 24 hours. The animals were observed for gross signs of systemic toxicity, dermal irritation, and death for 14 days. Animals were weighted 7 days after treatment. At the end of the 14day observation period, the rabbits were weighed, killed, and given a gross necropsy.

No deaths occurred during the observation period. No clinical changes were observed. The most frequently observed irritative effects included erythema and desquamation. Gross necropsies performed at the end of the study revealed no significant gross changes. The acute dermal $LD_{50}$ value was found to be greater than 2.0 g/kg in male and female New Zealand White rabbits. The compound was classified in Toxicity Category III by dermal administration.

Example 11

Primary Skin Irritation of 1-aza-3,7-dioxo-2,8-bicyclo-diisopropyl-5-ethyl (3.3.0) octane The primary skin irritation of the compound was evaluated in compliance with the conditions specified in the Regulation for the Enforcement of Federal Insecticide, Fungicide and Rodenticide Act (40 CFR 162). A small amount of the compound (0.5 ml) was applied to an intact skin site on six New Zealand White rabbits (three males and three females) and allowed to remain in contact with the skin for 4 hours. The sites were scored for erythema and edema and checked for tissue damage ½ hour after the end of the application period (4½ hour reading) and 19 hours (24-hour reading) and at 48 and 72 hours.

The Primary Irritation Index was found to be 2.7. No evidence of tissue damage (corrosion) was found. Mild irritation persisted 72 hours after application. The material is classified in Toxicity Category IV by dermal application.

Example 12

Primary Eye Irritation of 1-aza-3,7-dioxo-2,8-bicyclo-diisopropyl-5-ethyl (3.3.0) octane The primary skin irritation of the compound was evaluated in compliance with the conditions specified in the Regulation for the Enforcement of Federal Insecticide, Fungicide and Rodenticide Act (40 CFR 162). A small amount of the undiluted compound (0.1 ml) was applied to the right or left eye of six New Zealand White rabbits (one male and five females). The compound was allowed to remain without rinsing in the eyes of the animals. The eyes were graded for corneal changes, conjunctival changes, and changes in the iris one hour after application, and one, two, three, four, and seven days later.

The compound produced corneal opacity persisting for less than seven days and irritation persisting for seven days when applied without rinsing to the eyes of six New Zealand White rabbits. The material was classified in Toxicity Category II by ocular application.

While the invention is susceptible to various modifications and alternative forms, specific embodiments thereof have been shown by way of example and were herein described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

We claim:

1. A method of dehydrating a preparation including at least one pigment and at least one organic solvent, comprising intimately admixing with the preparation at least 0.5 mole of a moisture-scavenging compound for every mole of water to be dehydrated, the moisture-scavenging compound having the structure:

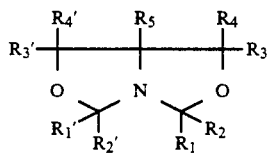

wherein: $R_1$ and $R_1'$ are individually selected from the group consisting of: methyl, branched or straight chain alkyl, and branched or straight chain alkanol; $R_2$, $R_3$, $R_4$, $R_2'$, $R_3'$, $R_4'$ are individually selected from the group consisting of: hydrogen, methyl, branched or straight chain alkyl, branched or straight chain alkanol, cyclic alkyl, and aryl; $R_5$ is selected from the group consisting of: methyl, methanol, branched or straight chain alkyl, and branched or straight chain alkanol.

2. The method of claim 1 including from 0.5 to about 2 moles of the compound for every mole of water in the preparation to be dehydrated.

3. The method of claim 1 wherein the preparation further includes a filler.

4. The method of claim 1 further including the step of intimately admixing a polyisocyanate with the preparation after the preparation has been dehydrated.

* * * * *